United States Patent [19]
Lee

[11] Patent Number: 6,073,359
[45] Date of Patent: Jun. 13, 2000

[54] HEIGHT MEASURING DEVICE

[76] Inventor: In Bok Lee, 800 Winding Way, River Vale, N.J. 07675

[21] Appl. No.: 09/047,428

[22] Filed: Mar. 25, 1998

[51] Int. Cl.[7] .............. G01B 3/10; G01B 3/22; A61B 1/00; B43L 7/00
[52] U.S. Cl. .............. 33/759; 33/512; 33/483; 33/832; 33/DIG. 1
[58] Field of Search .............. 33/512, 759, 783, 33/832, DIG. 1

[56] References Cited

U.S. PATENT DOCUMENTS

| | | | |
|---|---|---|---|
| 442,192 | 12/1890 | Lewis | 33/512 |
| 1,377,671 | 5/1921 | Dieckmann | 33/512 |
| 2,215,884 | 9/1940 | Runge | 33/512 |
| 2,736,099 | 2/1956 | Fischer | 33/169 R |
| 3,313,030 | 4/1967 | Heys | 33/169 R |
| 4,134,212 | 1/1979 | Allen | 33/169 R |
| 4,134,213 | 1/1979 | Kushmuk | 33/512 |
| 4,196,521 | 4/1980 | Hutchinson et al. | 33/169 R |
| 4,653,194 | 3/1987 | Kim | 33/429 |
| 4,654,978 | 4/1987 | Woldford, Jr. | 33/481 |
| 4,827,622 | 5/1989 | Makar | 33/770 |
| 4,854,049 | 8/1989 | Kuhtik | 33/464 |
| 5,361,504 | 11/1994 | Huang | 33/371 |
| 5,379,028 | 1/1995 | Chung | 340/692 |
| 5,402,585 | 4/1995 | Lund | 33/832 |

FOREIGN PATENT DOCUMENTS

| | | |
|---|---|---|
| 1206363 | 2/1960 | France . |
| 57-156517 | 9/1982 | Japan . |

*Primary Examiner*—Randy W. Gibson
*Attorney, Agent, or Firm*—Richard C. Litman

[57] ABSTRACT

A height measuring device having an elongated member with a substantially rectangular cross-section. A channel or groove is formed in the middle of the elongated member's wider side and substantially extends the entire length of the elongated member. A metal strip is attached to the inside surface of the groove. The metal strip engages a magnetic plate of a sliding bar which is movably positioned inside the groove and extends out of the elongated member forming a perpendicular angle with respect to the elongated member's surface. The sliding bar is part of a kit of measuring bars or blocks which can be aligned with the scales to measure the height of an individual. The measuring blocks contain magnetic plates attached to its periphery for placement adjacent to the bottom of the groove. The member is made of various materials and is vertically attached to a wall including a measuring tape with an adhesive attached to the member's outside surface.

13 Claims, 5 Drawing Sheets

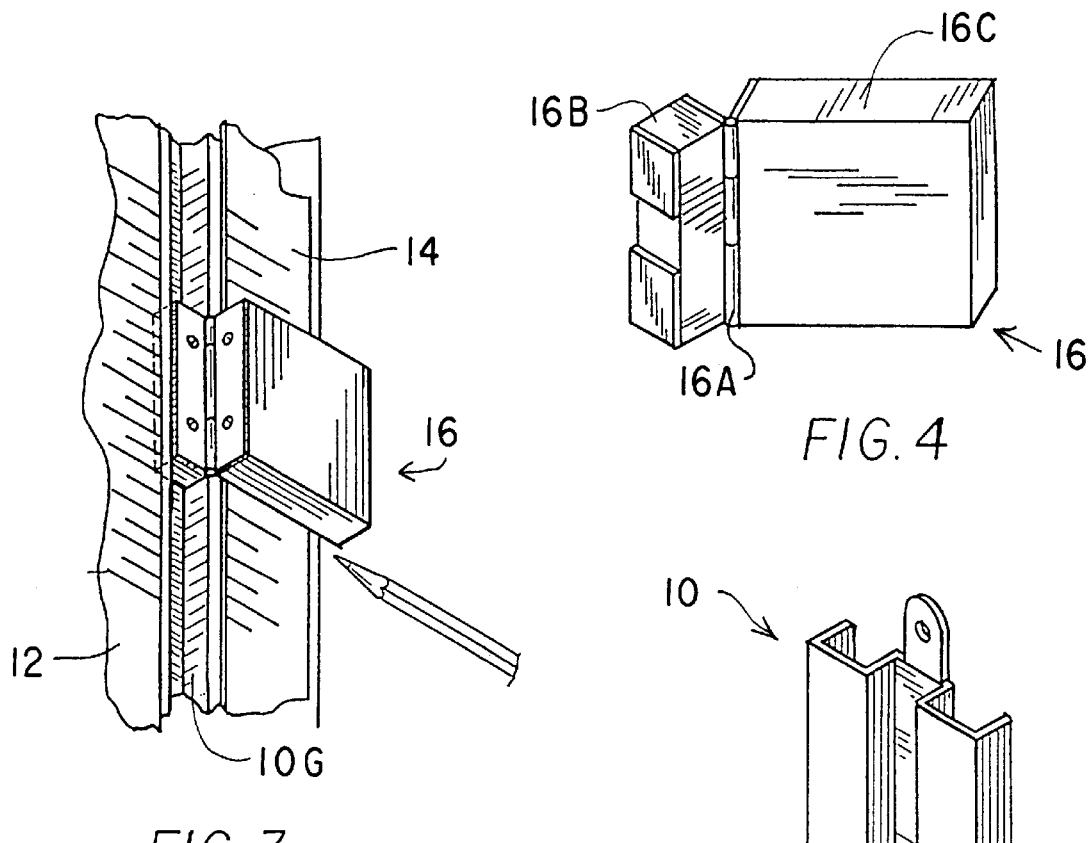
FIG. 3
FIG. 4
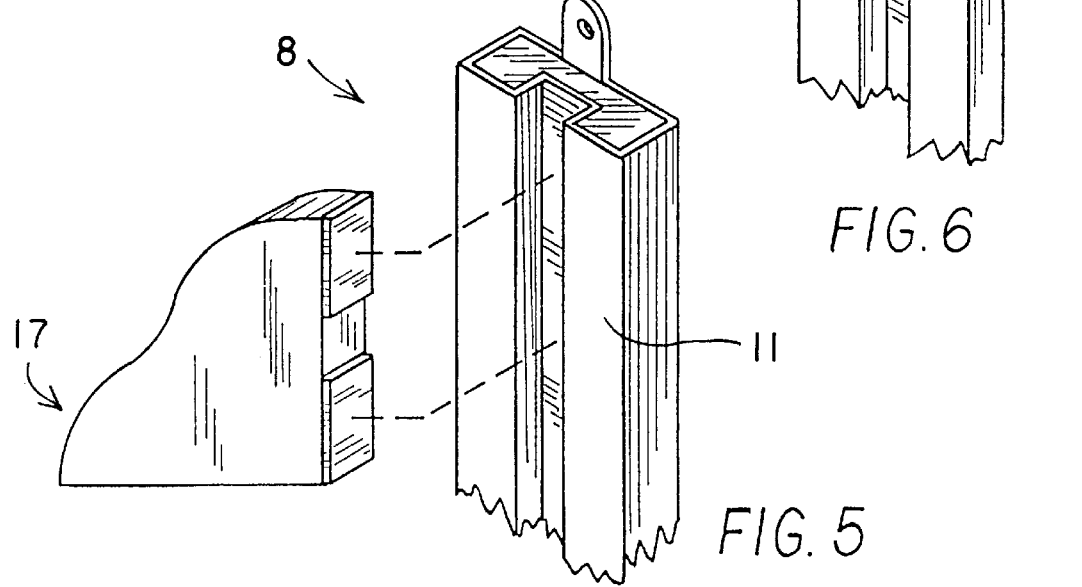
FIG. 5
FIG. 6

HEIGHT MEASURING DEVICE

BACKGROUND OF THE INVENTION

1. Field of the Invention

The present invention relates generally to measuring devices. More specifically, the invention is a portable human height measuring device for measuring and comparing the growth rate of different people.

2. Description of Related Art

Various measuring devices have been devised for measuring the heights of people and other measurable entities such as earth core samples and other objects which vary in size with time. The problem, however, with most of the conventional measuring devices is that height measurements of different people (i.e. infants, children, and adults) become quite difficult to measure because the conventional height measurement devices lack features which universally permit ease of use, portability and adaptability of the measurement device to each person.

For example, U.S. Pat. No. 4,134,212 issued to Allen discloses a growth measuring scale similar in purpose to the instant invention, namely to make height measurement comparisons. The growth measuring scale by Allen is an elongated graduated panel having a pivotally connected head bar which is movable from a vertical head locked position to a horizontal position. This device is structurally different from the instant invention in that the instant invention utilizes insertable magnetized height markers which are removable as herein described.

U.S. Pat. No. 4,196,521 issued to Hutchinson et al. discloses a conventional height measuring device which is typically used commercially in clinics and hospitals as a stand-alone measuring device. Unlike the instant invention, this device is quite heavy and difficult to transport manually. In addition, the device of Hutchinson is not adaptable for use on a wall or refrigerator as herein described.

U.S. Pat. Nos. 5,402,585 and 3,313,030 issued to Heys and Lund respectively disclose height measuring devices having similar conventional features as taught by Hutchinson et al., except that the respective height measuring devices of Heys and Lund are adaptable for use on walls. There is no disclosure by the patents of Heys and Lund for a magnetic height measuring device which is adaptable to walls and refrigerators as herein described. The patents by Kim (U.S. Pat. No. 4,653,194), Kuhtik (U.S. Pat. No. 4,854,049) and Kojima (JP 156517) respectively disclose measuring devices which include the principle use of magnetic attraction, but the disclosures teach measuring devices which are completely different from that of the instant invention.

U.S. Pat. No. 5,379,028 issued to Chung disclose a height measuring device with voice readout. Unlike the instant invention, Chung's height measurement device requires the use of digital circuitry including complex mechanisms for calibrating or linking circuitry to the device for proper height indication.

Other patents by Fischer (U.S. Pat. No. 2,736,099), Woldorf, Jr. (U.S. Pat. No. 4,654,978), Huang (U.S. Pat. No. 5,361,504) and Duceau et al. (FR 1206363) disclose measuring devices of general relevance, but the devices are unrelated to the height measuring device as herein described.

The height measuring device of the instant invention is different from the prior and related art, in that it provides a height measurement device which is easy to use and adaptable for use on walls and refrigerators for measuring and comparing the heights or growth rates of different people. The invention is unique in that it includes height markers which serve a dual role of being insertably and magnetically attached to the device for indicating heights of different people and for attracting children's interest in making height measurements in the form of educational magnetic block toys which are provided in the form of a kit.

In this regard, none of the above inventions and patents, taken either singly or in combination, is seen to describe the instant invention as claimed.

SUMMARY OF THE INVENTION

The height measuring device according to the present invention has an elongated member or frame with multiple configurations having a substantially rectangular cross-section. A rectangular groove is formed in the middle of the elongated member's wider side and substantially extends the entire length of the elongated member. The member is constructed of plastic, wood, heavy weight paper or metal and a metal strip is attached to the inside surface of the groove. The metal strip is engaged with a magnetic plate of a sliding bar which bar is movably positioned inside the groove and extends out of the elongated member forming a perpendicular angle with the elongated member's surface.

The sliding bar is part of a kit of a plurality of bars or blocks for indicating the measurement of an individual. The measuring blocks contain magnetic plates attached to its periphery adjacent to the bottom of the groove. The member can be vertically attached to a wall. A measuring tape with an adhesive backing is attached to the member's outside surface. The measuring blocks double as educational toys to attract the interest of children in making height measurements.

Accordingly, it is a principal object of the invention to provide a height measuring device for measuring the height of an individual.

It is another object of the invention to provide a height measuring device for measuring and comparing the height of different individuals.

It is a further object of the invention to provide a height measuring device for determining the growth rate of more than one individual.

Still another object of the invention is to provide a height measuring device which is light weight and portable for vertical attachment to a wall or refrigerator.

It is an object of the invention to provide improved elements and arrangements thereof in the height measuring apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

FIG. 3 is a fragmented, perspective view of the height measuring device according to the invention, illustrating height growth marking.

FIG. 4 is a perspective view of the magnetized measuring block according to the invention.

FIG. 5 is a fragmented, exploded perspective view of an alternate embodiment of the human measuring device according to the invention, illustrating an alternate design of the measuring block and frame.

FIG. 6 is a fragmented perspective view of an alternate design of the frame in FIG. 5 according to the invention.

Similar reference characters denote corresponding features consistently throughout the attached drawings.

DETAILED DESCRIPTION OF THE PREFERRED EMBODIMENTS

Figure 2:
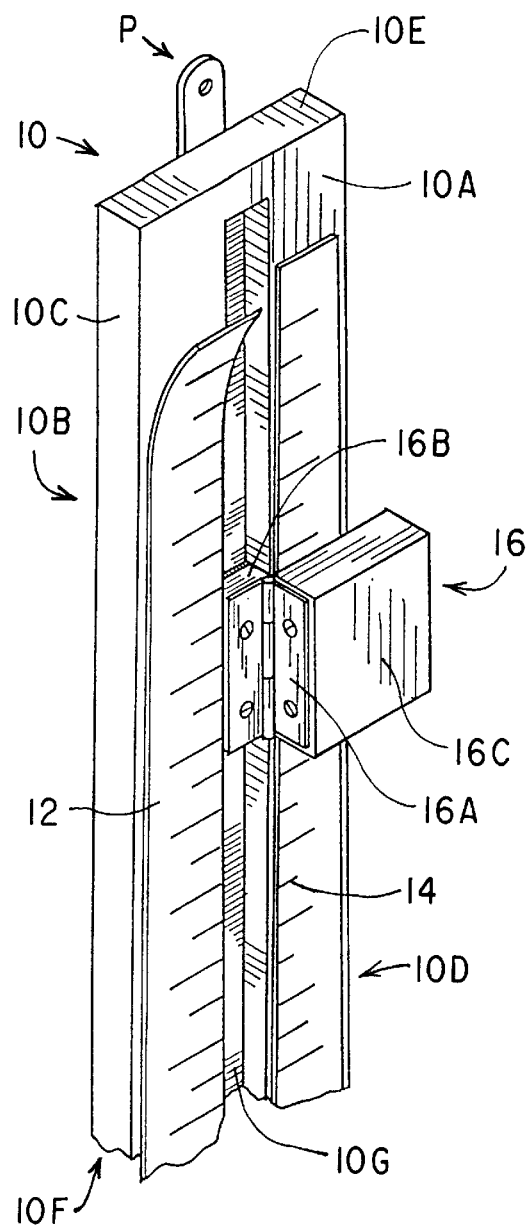
FIG. 2 is a fragmented, perspective view of the height measuring device according to the invention, illustrating the self adhesive measuring tape and magnetic hinged block.

The present invention is directed to a height measuring device for measuring and comparing the growth rate of different people. The preferred embodiments of the present invention are depicted in FIGS. 1–7, and is generally referenced by numeral 20.

As best seen in FIGS. 1–7, the height measuring device 20 comprises an elongated frame 10 having a front face 10a, back 10b and first and second sides 10c, 10d, a top 10e and a bottom 10f, left and right graduated scales 12,14 attached to the front face 10a and a substantially rectangular magnetic block 16 for movably aligning a height measurements along the scales 12,14. Once so aligned, as diagrammatically illustrated in FIG. 3, the block can be horizontally pivoted and used as a straight edge to mark the scale with a writing implement W by virtue of a hinge 16a. The frame 10 can be shaped to resemble different characters or configurations (i.e. animals, people, etc.) depending on personal preference.

Figure 1:
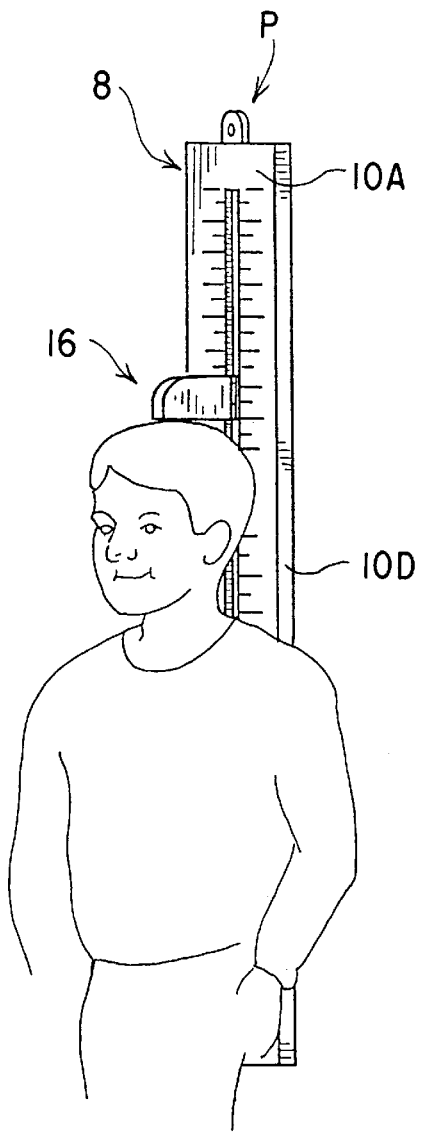
FIG. 1 is an environmental, perspective view of the human measuring device according to the invention.

As seen in FIGS. 1 and 2 at least, the frame 10 further comprises a centrally disposed rectangular recess 10g in the front face 10a which extends substantially along the longer length of the rectangular frame 10. The recess 10g has a metallic surface magnetically attracting the magnetic block 16. At least one graduated scale 12 and/or 14 is respectively disposed on the front face to the left and/or right of said recess 10g which is centrally disposed within the frame 10.

As illustrated in FIGS. 1, 2, 5 and 6, the frame 10 is adapted for hanging on a planar vertical surface by the attachment of a planar, semi-circular extension plate P. According to the preferred embodiment the planar surface can be a wall, or a surface of a refrigerator or freezer (not shown). In addition, the frame 10 of the measuring device can include metal, wood or plastic. With respect to attaching the measuring device 20 to a surface of a refrigerator or freezer, a number of magnets can be attached to the back portion of the frame (not shown) for proper use of the device.

The particular materials used to construct the frame 10 should be capable of accommodating the use of adhesives for attaching independent metal strips or graduated scales thereto. Any method can be use for producing the height measuring device according to invention such as injection molding. Other methods such as etching can also be used respectively to provide graduated scales for example made within the material of choice without the specific need for adhesives. It would be obvious to one of ordinary skill in the art to produce the intended results of the instant invention as herein described as a mere matter of design choice.

As diagrammatically illustrated in FIGS. 4, 5, 7, 9, 10 and 11, there are six embodiments of the magnetic block 16 according to the intended purpose of the invention.

In FIG. 4, the magnetic block 16, comprises a hinge 16a which attaches to a magnetic block portion 16b and to a non-magnetic block portion 16c. The hinge 16a is preferably attached by mechanical fasteners such as screws or adhesives. However, any fastener method available to one skilled in the relevant art, can be used so long as it provides the intended purpose of the invention as herein described. Another important feature of the hinged magnetic block 16 is that it allows a non-magnetic portion of the block to align with said left and right graduated scales for noting height or growth measurements.

Figure 7:
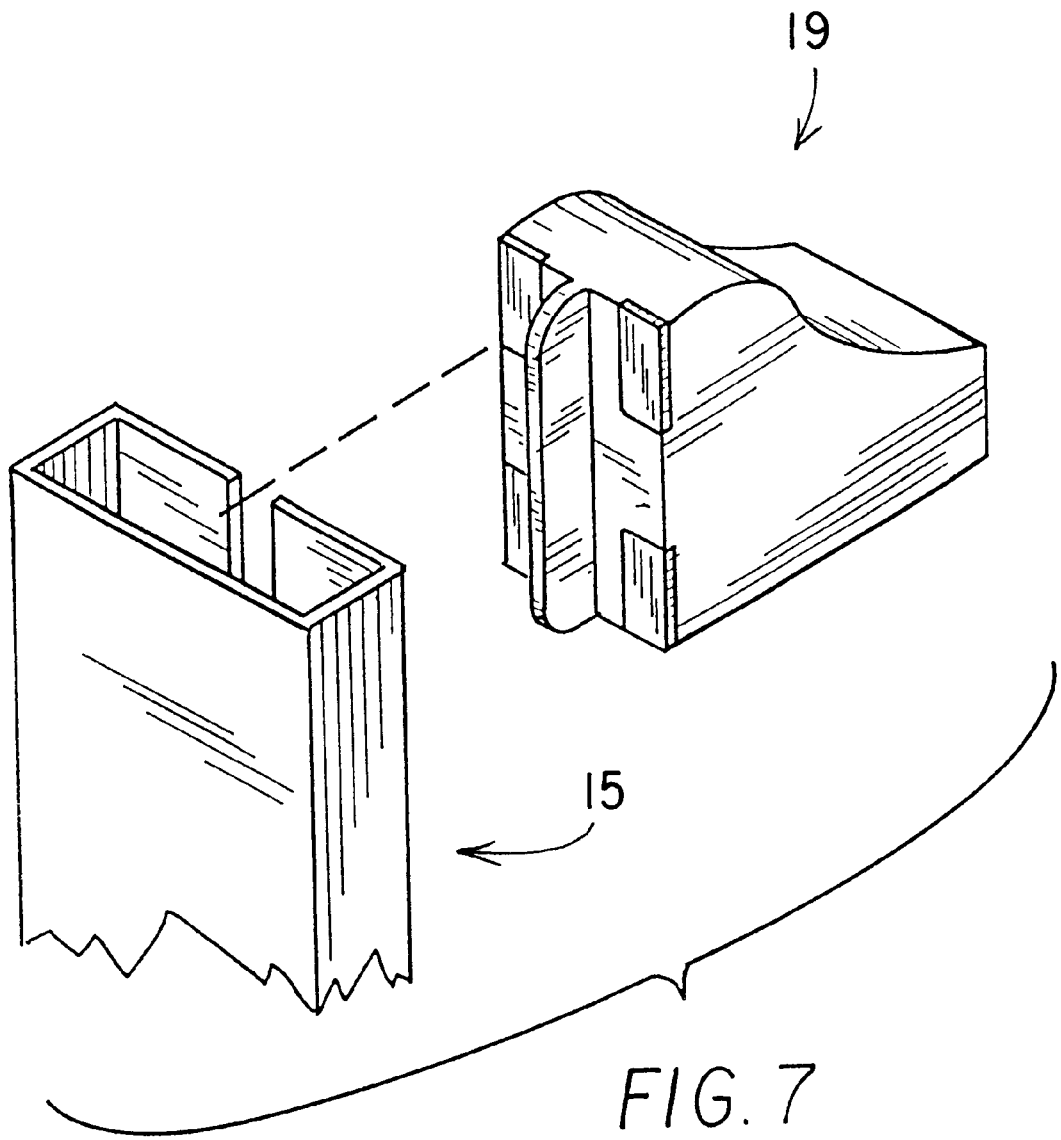
FIG. 7 is a fragmented, exploded perspective view of an insertable magnetized measuring block and frame according to the invention.
Figure 8:
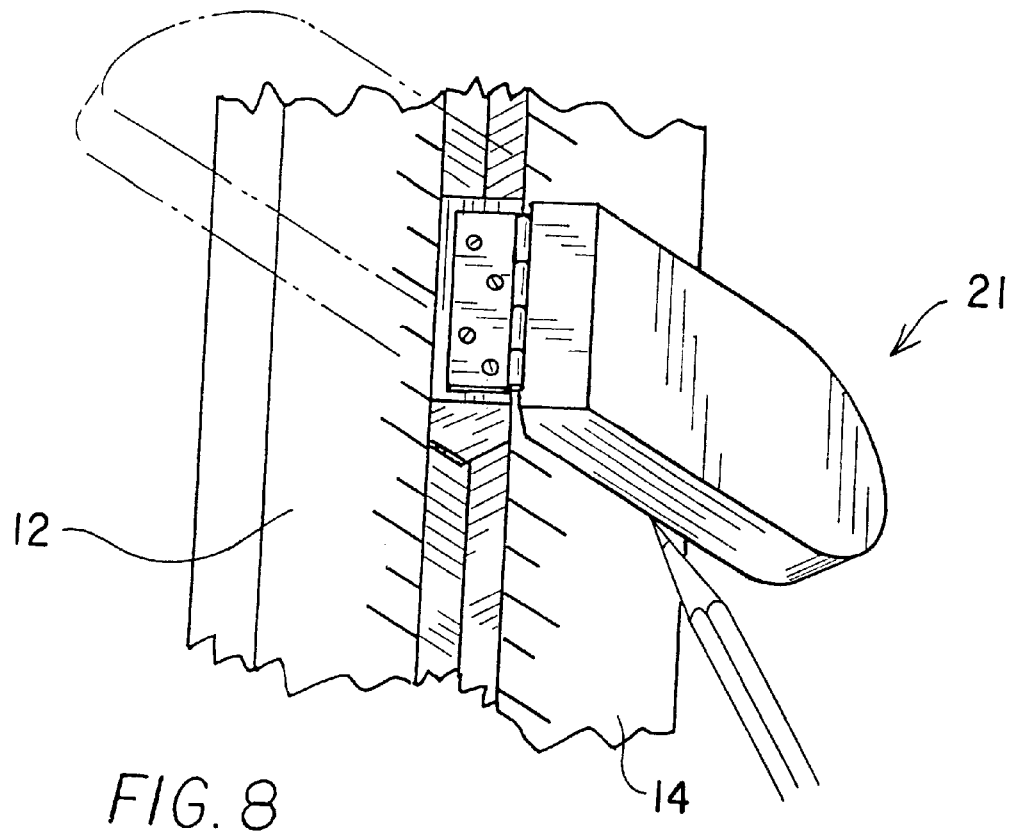
FIG. 8 is an alternate embodiment of the height measuring device according to the invention, illustrating an magnetized swivel measuring block.
Figure 9:
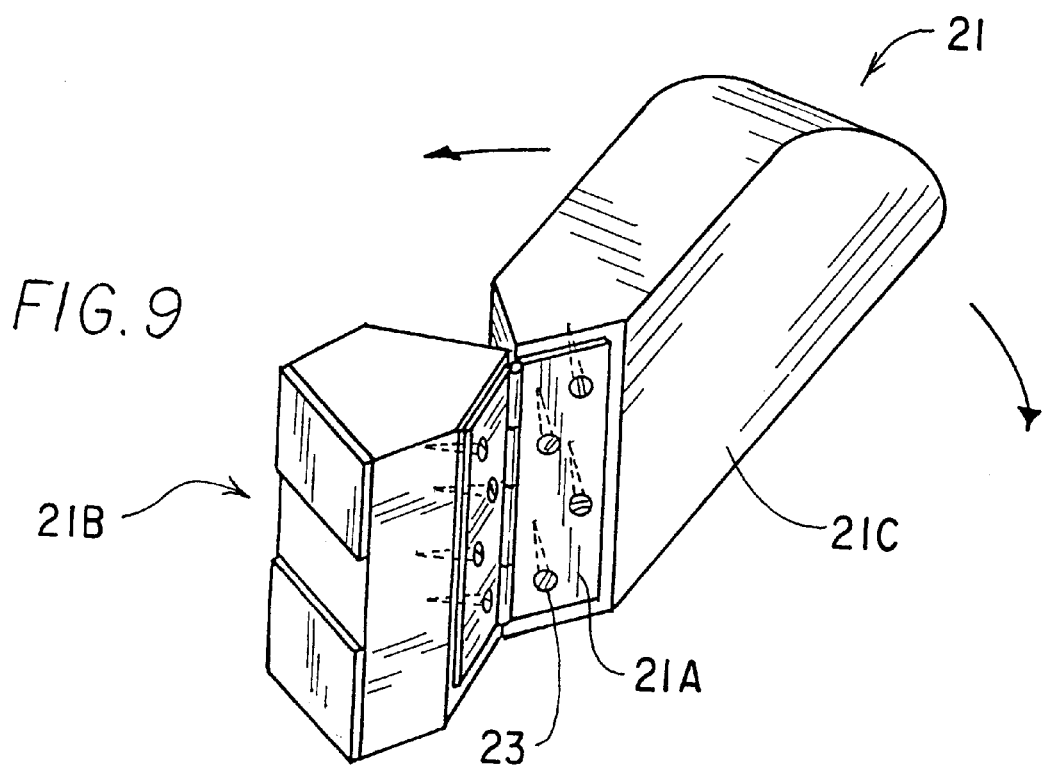
FIG. 9 is a perspective view of the magnetized swivel measuring block, illustrating the use of mechanical fasteners for attaching the hinge.

Other embodiments of the magnetic block 16, include a substantially rectangular shaped block with attached magnets for attachment to the frame 10 and for indicating a specific height measurement or growth rate as indicated by the graduated scales 12 and 14 for example. The height measuring device provides height measurements in units of inches and feet, but other units can be used depending on the users personal preferences. Units other than English units can be readily accommodated in the instant invention by the skilled artisan as a mere matter of routine skill in the art. FIGS. 5–7, 10 and 11 diagrammatically illustrate five alternative embodiments of the height measuring frame 10 for the respective different magnetic blocks according to the invention. Another version of the magnetic block assembly according to the invention includes an insertable lip portion 19 of the magnetic block 16, as shown in FIG. 7. FIGS. 8 and 9 illustrate an alternate embodiment of the human measuring device utilizing a swivel hinged magnetized block for indicating the height of a person. In FIG. 9, the magnetic block 16, comprises a hinge 16a which attaches to a magnetic block portion 16b and to a nonmagnetic block portion 16c. The swivel hinge 16a is preferably attached by mechanical fasteners 23 such as screws or adhesives. However, any fastener method available to one skilled in the relevant art, can be used so long as it provides the intended purpose of the invention as herein described. The swivel magnetized measuring block has the similar feature of the hinged magnetic block 16 of FIG. 4 in that it allows a non-magnetic portion of the block to align with at least one graduated scale on the left and/or right side of the centrally disposed recess for noting height or growth measurements.

Figure 10:
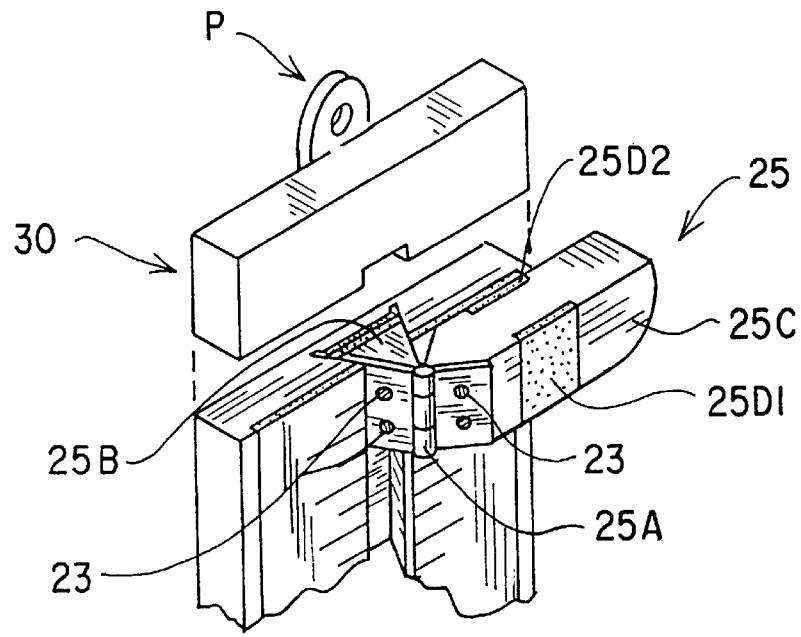
FIG. 10 is an alternate embodiment of the height measuring device according to the invention, illustrating a triangular shaped hinged magnetized measuring block.
Figure 11:
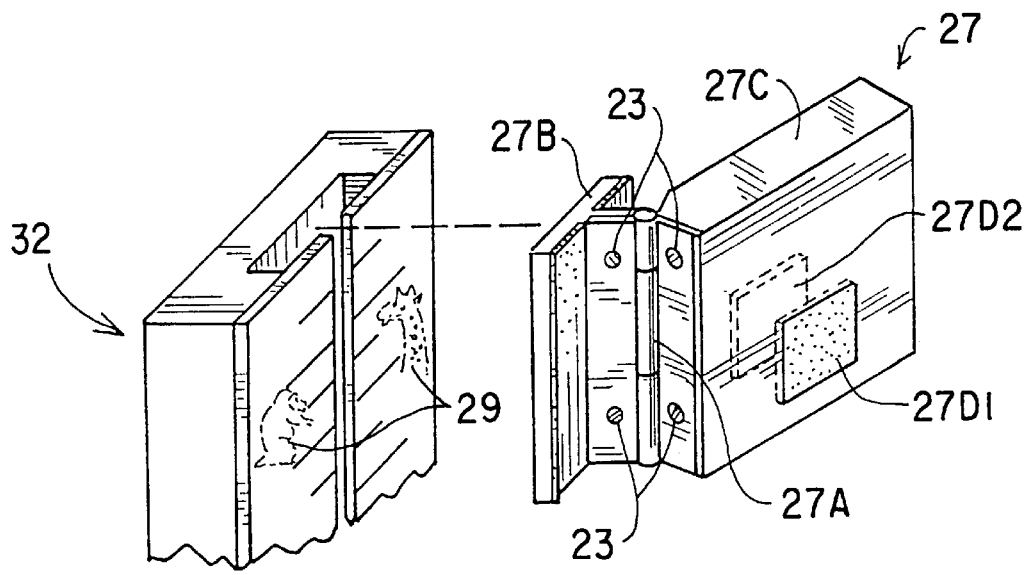
FIG. 11 is an alternate embodiment of the height measuring device according to the invention, illustrating a T-shaped hinged magnetized measuring block.

In FIG. 10, the magnetic block 25, comprises a hinge 16a which attaches to a triangular magnetic block portion 16b and to a magnetic block portion 16c. The hinge 16a is preferably attached by mechanical fasteners 23 such as screws or adhesives. However, any fastener method available to one skilled in the relevant art, can be used so long as it provides the intended purpose of the invention as herein described. The triangular magnetized measuring block has the similar feature of the hinged and swivel magnetic blocks 16 of FIGS. 4 and 9, except that magnetic patches 25d1 and 25d2 are attached to of the block 16c to align with said left and right graduated scales for noting height or growth measurements. In FIG. 11, the magnetic block 16, comprises a hinge 16a which attaches to a T-shaped magnetic block portion 16b and to a magnetic block portion 16c. The hinge 16a is similarly preferably attached by mechanical fasteners 23 such as screws or adhesives. However, any fastener method available to one skilled in the relevant art, can be used so long as it provides the intended purpose of the invention as herein described. The T-shaped magnetized measuring block 16 of FIG. 11 has the similar feature of the triangular shaped magnetic block 16 of FIG. 10, in that magnetic patches 25d1 and 25d2 are attached to the block 16c to align with said left and right graduated scales for noting height or growth measurements. In addition, various designs of favorite cartoon or animal characters 29 can be incorporated along the graduated scale as illustrated in FIG. 11 to capture a child's interest or attention for making height measurements according to the invention. A removable cap member 30 including extension plate P is an optional feature which magnetically attaches to the top 10c of the frame 10. This feature can also be included with the frame 10 of the embodiment shown in FIG. 11.

Other advantages of the instant invention include the alternative use of the magnetic blocks 16 shown in FIGS. 4, 5, 7 and 9–11 as toys for children (not shown). The blocks can be designed to resemble a child's favorite cartoon or otherwise characters for personal appeal. The use of the magnetic block according to the invention in the height measuring device can serve to peak children's interest in making height measurements according to the invention.

It is to be understood that the present invention is not limited to the sole embodiment described above, but encompasses any and all embodiments within the scope of the following claims.

What is claimed is:

1. A height measuring device comprising:
   an elongated frame adapted to be attached to a vertical supporting surface, said frame having a length and including a front face;
   a recess centrally disposed in the front face of said frame, said recess including a metallic surface and extending substantially along the length of said frame;
   at least one graduated scale attached to the front face of the frame adjacent said recess;
   a magnetic block movably disposed within said recess; and
   a block member hingedly connected to said magnetic block, said block member being horizontally pivotably and having a straight edge for aligning with said at least one graduated scale.

2. The height measuring device according to claim 15, wherein said frame is shaped in different configurations and includes a means for hanging said frame on the vertical supporting surface.

3. The height measuring device according to claim 1, wherein said at least one graduated scale includes a left and a right graduated scale respectively labelled in units of inches and feet.

4. The height measuring device according to claim 2, wherein said frame is made of wood.

5. The height measuring device according to claim 2, wherein said frame is made of plastic.

6. The height measuring device according to claim 2, wherein said frame is metallic.

7. The height measuring device according to claim 1, wherein said at least one graduated scale is adhesively attached.

8. The height measuring device according to claim 1, wherein said at least one graduated scale is etched within the front face of the frame.

9. The height measuring device according to claim 1, wherein said magnetic block and said recess have T-shaped cross-sectional configuration.

10. The height measuring device according to claim 1, wherein said magnetic block has a triangular cross-sectional configuration.

11. The height measuring device according to claim 9, wherein said frame is metallic and said block member includes magnetic patches attached to opposite sides thereof.

12. The height measuring device according to claim 10, wherein said frame is metallic and said block member includes magnetic patches attached to opposite sides thereof.

13. A height measuring device comprising:
   an elongated frame adapted to be attached to a vertical supporting surface, said frame having a length and including a front face;
   a recess centrally disposed in the front face of said frame, said recess including a metallic surface and extending substantially along the length of said frame;
   at least one graduated scale attached to the front face of the frame adjacent said recess; and
   a magnetic block movably disposed within said recess.

* * * * *